United States Patent

Bott et al.

[11] 4,370,491
[45] Jan. 25, 1983

[54] CONTINUOUS PREPARATION OF ACETIC ACID ESTERS

[75] Inventors: Kaspar Bott, Wachenheim; Gerd Kaibel, Lampertheim; Herwig Hoffmann, Frankenthal; Rudolf Irnich, Bobenheim; Eberhard Schaefer, Ludwigshafen, all of Fed. Rep. of Germany

[73] Assignee: BASF Aktiengesellschaft, Ludwigshafen, Fed. Rep. of Germany

[21] Appl. No.: 263,470

[22] Filed: May 14, 1981

[30] Foreign Application Priority Data

May 23, 1980 [DE] Fed. Rep. of Germany ....... 3019767

[51] Int. Cl.$^3$ ...................... B01D 3/36; C07C 67/02; C07C 67/06
[52] U.S. Cl. .................... 560/234; 560/248; 203/60; 203/63; 203/98; 203/DIG. 6; 422/187
[58] Field of Search .............................. 560/234, 248; 203/DIG. 6, 63, 60, 98; 422/187

[56] References Cited

U.S. PATENT DOCUMENTS

| | | | |
|---|---|---|---|
| 1,433,308 | 10/1922 | Steffens | 560/234 |
| 1,491,076 | 4/1924 | Burghart | 560/234 |
| 2,555,606 | 6/1951 | Potts | 203/DIG. 6 |
| 2,707,165 | 4/1955 | MacLean et al. | 203/DIG. 6 |
| 3,241,926 | 3/1966 | Parker et al. | 203/DIG. 6 |
| 3,579,309 | 5/1971 | Sennewald et al. | 560/234 |
| 3,963,446 | 6/1976 | Miller | 203/DIG. 6 |

Primary Examiner—Wilbur L. Bascomb, Jr.
Attorney, Agent, or Firm—John H. Shurtleff

[57] ABSTRACT

A process for the preparation of acetic acid esters $CH_3—CO—O—R^1$ (I, $R^1$ = an organic radical other than methyl and ethyl) by alkali-catalyzed trans-esterification of an acetic acid ester $CH_3—CO—O—R^2$ (II, $R^2$ = methyl or ethyl) with an alcohol $R^1—OH$ (III), accompanied by elimination of the alcohol $R^2—OH$ (IV), wherein (a) the trans-esterification reaction is carried out in the middle section $K_M$ of a distillation column K, the alcohol III being fed as liquid into the upper zone and the ester II into the lower zone of $K_M$, (b) the alkaline catalyst is introduced into the upper part $K_U$ of K, (c) the alcohol IV, or a mixture of IV and the ester II, is taken off the top of the column, (d) the mixture obtained from (c) (unless the alcohol IV alone is obtained) is separated in the column section $K_U$ or in a stripper column $K_S$ into IV and the azeotrope of II and IV, and the latter is recycled to the lower zone of $K_M$, (e) the ester I is taken as vapor or liquid from the lower zone of the lower section $K_L$ of K and (f) the catalyst is either removed, or recycled to $K_U$, in a conventional manner.

5 Claims, 1 Drawing Figure

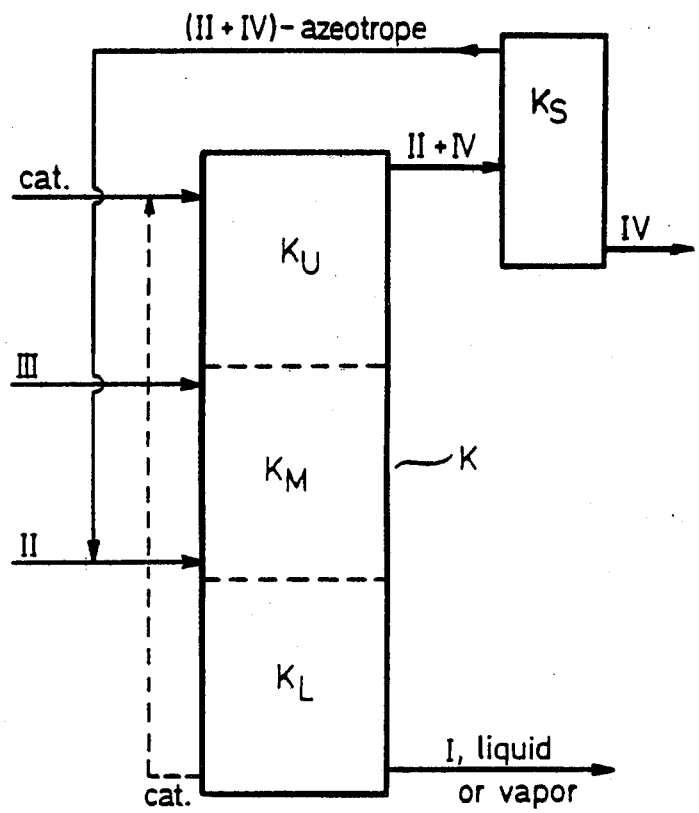
$$CH_3-CO-O-R^2 + R^1-OH \xrightarrow{cat.} CH_3-CO-O-R^1 + R^2-OH$$
$$\text{II} \qquad\qquad \text{III} \qquad\qquad\qquad \text{I} \qquad\qquad \text{IV}$$

CONTINUOUS PREPARATION OF ACETIC ACID ESTERS

The present invention relates to an improved process for the preparation of acetic acid esters of the general formula I $$CH_3-CO-O-R^1 \qquad \text{I}$$

where $R^1$ is an organic radical, other than methyl or ethyl, by alkali-catalyzed trans-esterification of an acetic acid ester of the general formula II $$CH_3-CO-O-R^2 \qquad \text{II}$$

where $R^2$ is methyl or ethyl, with an alcohol III $$R^1-OH \qquad \text{III}$$

accompanied by elimination of the alcohol IV $$R^2-OH \qquad \text{IV,}$$

in accordance with the following equation:

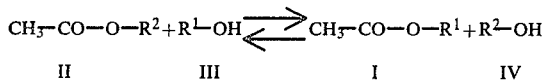

This trans-esterification process is prior art, except for the improvement according to the invention. In principle, the process has hitherto been carried out by allowing the reaction to proceed approximately to equilibrium, after which the reaction mixture was separated into its components by distillation. However, a great disadvantage of this method is that methanol and methyl acetate, as well as ethanol and ethyl acetate, and in most cases also the alcohol $R^1$—OH and its acetate, form azeotropes. For this reason, working up of the trans-esterification mixtures by distillation presents considerable difficulties, and furthermore it is not economically possible to shift the esterification equilibrium in the direction of the desired ester I by continuous removal of the alcohol $R^2$—OH, since the starting ester II is thereby always also removed from the reaction (as an azeotrope with IV).

It is an object of the present invention to overcome these disadvantages in a continuous process, so that the azeotrope of I and III no longer proves troublesome and that the formation of the azeotrope of II and IV is also completely suppressed or, where this is not possible, these azeotropes are harmoniously integrated into the trans-esterification process.

We have found that this object is achieved by an improved process for the preparation of the acetic acid ester I, in accordance with the general principle presented at the outset, in which process (a) the trans-esterification reaction is carried out in the middle section $K_M$ of a distillation column K, the alcohol III being fed as liquid into the upper zone and the ester II into the lower zone of $K_M$, using 1 mole up to not more than 3 moles of the ester II per mole of the alcohol III, (b) the alkaline catalyst is introduced into the upper part $K_U$ of K, (c) the alcohol IV, or a mixture of IV and the ester II, is taken off the top of the column, (d) the mixture obtained from (c) (unless the alcohol IV alone is obtained) is separated in the column section $K_U$ or in a stripper column $K_S$ into IV and the azeotrope of II and IV, and the latter is recycled to the lower zone of $K_M$, (e) the ester I is taken as vapor or liquid from the lower zone of the lower section $K_L$ of K and (f) the catalyst is either removed, or recycled to $K_U$, in a conventional manner.

The process will be explained in more detail with reference to the FIGURE. The trans-esterification reaction takes place essentially in the middle section $K_M$ of the column K, with the alcohol III and the ester II travelling in counter-current. Here, the desired ester I is formed and, being a higher-boiling substance, passes into the lower section $K_L$ of the column. To prevent a mixture of I and III being formed in the lower section $K_L$, it is necessary to ensure that the alcohol III reacts completely. This is achieved by selecting appropriately high residence times in $K_M$ and/or employing the ester II in stoichiometric excess over the alcohol III. However, this excess is in general not more than 0.1-2 moles per mole of III. Thus, the present invention requires the use of from 1 mole to not more than 3 moles of the ester II per mole of the alcohol III.

If the ester II is employed pure, and not in excess over III, it generally reacts completely, so that virtually the pure alcohol IV, or a mixture containing only a small amount of II, is obtained at the top of the column. The fractionation in $K_U$, or the additional distillation in $K_S$, is then superfluous; either IV is use for any desired purpose or, which is particularly advantageous, it is recycled to the synthesis stage (not shown in the Figure) of II, since methyl acetate is usually prepared by carbonylation of methanol and ethyl acetate by a Tishtshenko reaction from ethanol. In both syntheses, small amounts of the ester II of course do not interfere.

If, however, II is employed in excess over III, or if II still contains appreciable amounts of IV, as is the case in practice, a mixture of IV with relatively large amounts of II is obtained at the top of the column. This mixture is separated, in the column $K_S$, or in the column section $K_U$, into the pure alcohol IV and the azeotrope of IV and II. The pure alcohol IV can then be re-used for any desired purpose or be recycled to the synthesis of II, and the azeotrope is recycled to the lower zone of $K_M$.

The alkaline catalyst used is preferably an alkali metal alcoholate, especially Na—O—$R^2$ or K—O—$R^2$, in the form of an 0.1-0.5% strength by weight solution in the alcohol $R^2$—OH (IV), the amount of the catalyst advantageously being from 0.05 to 1 mole %, based on the alcohol III employed.

Since some of the alcohol III also passes into the upper column section $K_U$, the trans-esterification can, to a slight extent, also proceed there. For this reason, it is advisable to introduce the catalyst into the upper zone of $K_U$. For experimental purposes, however, it mostly suffices to introduce the catalyst into the column together with the alcohol III.

If the ester I is taken as vapor from $K_L$, a catalyst-containing solution collects in the bottom, and can be recycled. Since, however, the catalyst is usually consumed in the course of the trans-esterification reaction, with formation of the less active alkali metal acetate, it is in general more advantageous to discard the catalyst-containing bottom product.

If the ester I is taken off as liquid, the catalyst is removed together with the ester. In that case, the ester must be purified by washing it with water or with dilute acid. Where the ester I is taken off as liquid, it is of course also possible to free this liquid from catalyst by distillation in a stripper column.

The trans-esterification process according to the invention can in principle be used to prepare any desired ester I, provided it, and the corresponding alcohol III, are liquid under the reaction conditions. The radicals $R^1$ in I and III can accordingly be aliphatic, cycloaliphatic, araliphatic and aromatic radicals of up to 12 carbon atoms, which radicals can, in turn, contain inert substituents, such as halogen or ether or polyether groups. Particularly important esters I are those which are employed as solvents. These esters are derived from $C_2$-$C_{12}$-alkanols and from glycol ethers or polyglycol ethers of the type $R'$—O—$(A—O)_n$—H, where $R'$ is $C_1$-$C_4$-alkyl, A is ethylene or 1,2-propylene and n is from 1 to 4. A further category of important esters I comprises those used as fragrances and flavorings. Such esters are derived, for example, from amyl alcohol, isoamyl alcohol, benzyl alcohol and terpene alcohols, such as linalool and citronellol.

The centerpiece of the column K is its middle section $K_M$, in which the trans-esterification reaction predominantly takes place. This column section, which should in general have from 8 to 20 theoretical plates, is preferably in the form of a bubble-cap tray column, valve tray column or perforated tray column, since these types make it possible to obtain long residence times, such as are required in most cases for the trans-esterification reaction.

In many cases, however, packed columns also suffice as the column section $K_M$. The upper column section $K_U$ and the lower column section $K_L$, on the other hand, serve principally to effect separations which are not particularly difficult, and therefore simple types of column such as packed columns as a rule suffice. However, it may be advisable to design these column sections as well as bubble-cap tray columns, valve tray columns or perforated tray columns, since thereby the division between the three column sections can be made flexible and easily adaptable to very diverse trans-esterification problems. In general, $K_U$ and $K_L$ should have from 3 to 15 theoretical plates.

It is advantageous to take off the product, ie. the ester I, from $K_L$ as a vapor side-stream, since the ester is thereby directly obtained in a pure form and its heat of condensation can be utilized to vaporize the ester II employed. Of course, the ester I can equally successfully also be distilled, or fractionated, in a stripper column.

In principle, the trans-esterification process according to the invention can be carried out under any pressure, but it is preferred to work under atmospheric pressure or under a slightly superatmospheric pressure (up to about 3 bar), which makes possible the condensation of the low-boiling ester II and alcohol IV by means of normal cooling water.

EXAMPLE

Preparation of n-butyl acetate from methyl acetate

An experimental column with about 50 theoretical plates was used to prepare n-butyl acetate by trans-esterifying methyl acetate with n-butanol under atmospheric pressure. The column was 3 m high, had an internal diameter of 5 cm, and was packed with wire mesh rings 0.5 cm in diameter.

At the level of the 15th plate from the bottom, an azeotropic mixture of 328 g/h of methyl acetate and 82 g/h of methanol was introduced as vapor, at 91° C., whilst at the level of the 35th plate (84° C.) a solution of 112 g/h of n-butanol and 0.5 g/h of K butylate was fed into the column. The middle section $K_M$ of the column was accordingly defined by plates 15 and 35.

Using a reflux ratio of 5, a mixture of 129 g/h of methanol and 219 g/h of methyl acetate was obtained at the top of the column (54° C.) and this mixture was separated, in a stripper column (35 theoretical plates), into the azeotrope of 55 g/h of methanol and 219 g/h of methyl acetate, in vapor form, and pure liquid methanol (74 g/h). The azeotrope was recycled as vapor to plate 15 of the column.

At the lower end of the column (129° C.), 169 g/h of n-butyl acetate, still containing about 2% by weight of n-butanol, were taken off as vapor. In the bottom, 5 g/h of n-butyl acetate, containing the catalyst, were formed. This bottom product was not subjected to any further working up.

It follows that the n-butyl acetate was obtained in 98% purity and in a yield of 97%.

We claim:

1. In a process for the preparation of an acetic acid ester of the formula $$CH_3—CO—O—R^1 \qquad \qquad I$$

where $R^1$ is an organic radical other than methyl or ethyl, by alkali-catalyzed trans-esterification of an acetic acid ester of the formula $$CH_3—CO—O—R^2 \qquad \qquad II$$

where $R^2$ is methyl or ethyl, with an alcohol $$R^1—OH \qquad \qquad III$$

accompanied by removal of the alcohol $$R^2—OH \qquad \qquad IV,$$

the improvement which comprises:
   (a) carrying out the trans-esterification reaction in the middle section $K_M$ of a distillation column K, the alcohol III being fed as liquid into the upper zone and the ester II into the lower zone of $K_M$, using 1 mole up to not more than 3 moles of the ester II per mole of the alcohol III,
   (b) introducing the alkaline catalyst into the upper part $K_U$ of the column K,
   (c) separating a mixture of the alcohol IV and the ester II obtained in the upper part $K_U$ of the column into the alcohol IV alone and an azeotropic mixture of II and IV, recycling said azeotropic mixture to the lower zone of $K_M$, and
   (d) withdrawing the ester I from the lower zone of the lower section $K_L$ of the column K.

2. A process as claimed in claim 1 wherein the ester II is used in a stoichiometric excess over the alcohol III, sufficient to ensure that said alcohol III reacts completely.

3. A process as claimed in claims 1 or 2 wherein the alcohol IV is separated from the ester II in the column section $K_U$ and taken off the top of the column alone.

4. A process as claimed in claims 1 or 2 wherein a mixture of the alcohol IV with the ester II is taken off from the top of the distillation column K, separated in a separate stripper column $K_S$ into the alcohol IV and said azeotropic mixture of II and IV.

5. A process as claimed in claims 1 or 2 wherein the catalyst is introduced into the upper zone of the column section $K_U$.

* * * * *